US010258991B2

(12) United States Patent
Thei et al.

(10) Patent No.: US 10,258,991 B2
(45) Date of Patent: Apr. 16, 2019

(54) HIGH SENSITIVITY MULTICHANNEL DETECTION DEVICE (71) Applicant: ELEMENTS S.R.L., Cesena (IT)

(72) Inventors: Federico Thei, Cesena (IT); Michele Rossi, Cesena (IT); Marco Bennati, Cesena (IT); Francesca Manzoni, Cesena (IT)

(73) Assignee: ELEMENTS S.R.L., Cesena (IT)

( * ) Notice: Subject to any disclaimer, the term of this patent is extended or adjusted under 35 U.S.C. 154(b) by 68 days.

(21) Appl. No.: 15/118,087

(22) PCT Filed: Feb. 13, 2015

(86) PCT No.: PCT/IT2015/000039
§ 371 (c)(1),
(2) Date: Aug. 10, 2016

(87) PCT Pub. No.: WO2015/121887
PCT Pub. Date: Aug. 20, 2015

(65) Prior Publication Data
US 2016/0354786 A1 Dec. 8, 2016

(30) Foreign Application Priority Data
Feb. 14, 2014 (IT) .............................. RM2014A0066

(51) Int. Cl.
B01L 9/00 (2006.01)
G01N 27/327 (2006.01)
G01N 27/414 (2006.01)

(52) U.S. Cl.
CPC .......... *B01L 9/527* (2013.01); *G01N 27/3273* (2013.01); *G01N 27/4145* (2013.01);
(Continued)

(58) Field of Classification Search
CPC ............... B01L 9/527; B01L 2200/027; B01L 2200/04; B01L 2200/10; B01L 2300/043;
(Continued)

(56) References Cited

U.S. PATENT DOCUMENTS

| 5,955,028 | A | 9/1999 | Chow |
| 6,153,069 | A | 11/2000 | Pottgen et al. |

(Continued)

FOREIGN PATENT DOCUMENTS

| WO | 96/30752 A1 | 10/1996 |
| WO | 01/33207 A1 | 5/2001 |

OTHER PUBLICATIONS

International Search Report and Written Opinion for International application No. PCT/IT2015/000039, Date of completion Jul. 1, 2015, dated Jul. 17, 2015.

(Continued)

*Primary Examiner* — Robert J Eom
(74) *Attorney, Agent, or Firm* — Steinfl + Bruno LLP (57) ABSTRACT A detection device of a sample to be examined is described, including a processing module, a detecting module, connected to the processing module, a support, in which the sample to be examined can be placed, the support including a plurality of sensors, preferably biosensors and/or nanosensors, and being insertable within the detecting module, and a containment enclosure including a body, which is arranged within the processing module, and a sensor portion, in which the detecting module is arranged. The processing module includes a processing unit having a plurality of processing channels and a processor, each one of the processing channels being connected to one respective of the sensors and being adapted to amplify and to filter the signals of the sensors, the processor processing the signals amplified and filtered by the processing channels.

17 Claims, 6 Drawing Sheets (52) U.S. Cl.
CPC ..... *G01N 27/4146* (2013.01); *G01N 27/4148* (2013.01); *B01L 2200/027* (2013.01); *B01L 2200/04* (2013.01); *B01L 2200/10* (2013.01); *B01L 2300/043* (2013.01); *B01L 2300/0636* (2013.01); *B01L 2300/0645* (2013.01); *B01L 2300/0819* (2013.01); *B01L 2400/0406* (2013.01)

(58) Field of Classification Search
CPC ..... B01L 2300/0636; B01L 2300/0645; B01L 2300/0819; B01L 2400/0406; G01N 27/3273; G01N 27/4145; G01N 27/4146; G01N 27/4148
See application file for complete search history.

(56) References Cited

U.S. PATENT DOCUMENTS

| | | |
|---|---|---|
| 6,197,503 B1 | 3/2001 | Vo-Dinh et al. |
| 2002/0177135 A1 | 11/2002 | Doung et al. |
| 2005/0058990 A1* | 3/2005 | Guia ................ G01N 33/48728 435/5 |
| 2006/0160205 A1* | 7/2006 | Blackburn .......... B01F 13/0059 435/287.2 |
| 2007/0263046 A1 | 11/2007 | Iwasa et al. |
| 2009/0026082 A1 | 1/2009 | Rothberg et al. |
| 2009/0114044 A1 | 5/2009 | Godfrey et al. |
| 2013/0321044 A1* | 12/2013 | Jordan ................ H03K 17/162 327/141 |

OTHER PUBLICATIONS

Italian Search Report for Italian Application No. ITRM2014000066, Date of completion Sep. 25, 2014.

Walter Kester, et al., "Grounding in Mixed Signal Systems," Hardware Design Techniques, Oct. 7, 2009, pp. 10.1-10.14.

\* cited by examiner

HIGH SENSITIVITY MULTICHANNEL DETECTION DEVICE

CROSS-REFERENCE TO RELATED APPLICATIONS

The present application is the U.S. National Stage of International Patent Application No. PCT/IT2015/000039 filed on Feb. 13, 2015 which, in turn, claims priority to Italian Application No. RM2014A000066 filed on Feb. 14, 2014.

The present invention relates to a high sensitivity multichannel detection device.

More specifically, the invention concerns a device of the above kind, which is fully enclosed in a compact metal housing with electromagnetic protection function, designed to house a card containing sensors (or biosensors), by which it is possible to carry out the observations or the measurements.

In the following, the description will be directed to the detection of ion channels, but it is clear that the same should not be considered limited to this specific use.

As it is well known currently ion channels are responsible for the exchange of transmembrane proteins between intra- and extra-cellular environments. Ion channels play an essential role in many biological processes and their dysfunction are involved in many diseases or serious illnesses.

Therefore, ion channels are under study for the realization and the preparation of many pharmaceutical compounds.

The capacity of ion channels to respond to different chemical-physical stimulations has stimulated the design of hybrid sensors, in which they are adopted as detection unit. This approach has already been used for the detection of molecules in solution and for DNA sequencing.

For biological purposes, it is essential to characterize the electrical behavior of the ion channel with high accuracy and precision.

This is achieved by the low noise acquisition equipment, capable of amplifying the currents of the ion channels that are of the order of picoamperes.

Current commercially available amplifiers capable of detecting the response of the ion channels provide bulky instrumentation and are limited in the number of channels simultaneously acquired due to the limitations of the discrete electronic architecture, with which they are manufactured.

It is evident how this procedure is costly in terms of efficiency of use, as well as commercial.

A further problem of the portable detection devices according to the prior art is given by the infiltration of liquids and solutions to be tested towards the electronic components, assembled on the printed circuit, on which there are the electronic components. This limits a very much their diffusion.

In light of the above, it is, therefore, object of the present invention to propose a high sensitivity multichannel detection system, which presents reduced dimensions, so as to allow the portability, and enabling accurate multichannel measures.

Another object of the invention is to provide a packaging that allows easy implementation of the measures and an optimum isolation of the printed circuit from the infiltration of liquid solutions to be examined.

These objects are obtained by the combination of a compact multi-channel system for reading the signals of the order of nanoamperes or picoamperes (pA or nA) from sensors coupled to devices that require the use of fluids. This implies both a separation of the "wet" part of the detection system from the electronics, and appropriate measures of electromagnetic shield (shielding) in order to optimize the signal/noise ratio.

It is therefore specific object of the present invention a detection device of a sample to be examined, comprising a processing module, a detecting module, connected to said processing module, a support, in which said sample to be examined can be placed, said support comprising a plurality of sensors, preferably biosensors and/or nanosensors, and being insertable within said detecting module, and a containment enclosure comprising a body, which is arranged within said processing module, and a sensor portion, in which said detecting module is arranged, characterized in that said processing module comprises a processing unit having a plurality of processing channels and a processor, each one of said processing channels being connected to one respective of said sensors and being adapted to amplify and to filter the signals of said sensors, said processor processing said signals amplified and filtered by said processing channels.

Always according to the invention, said processing module could be placed in said body of said containment enclosure, could be provided with a printed circuit board, in which an input connector is arranged, which has a plurality of terminals, preferably spring type, and an output connector, preferably USB type, connected to said processor, for the connection to a personal computer or processor, said containment enclosure preferably being made of conductive material, such as metal or the like.

Still according to the invention, each one of said processing channels could comprise an analog part, which includes an amplifier having an input connected to said input connector, an adder, interposed between said amplifier and a differentiator or active high-pass filter, and a digital part, which includes an analog to digital converter, having its output connected to said processor, and a second digital to analog converter, having its input connected to said processor and the output connected both to said adder, and to the input of said amplifier, so as to realize a control system of the potential applied to the input connector.

Further according to the invention, said processing channels, preferably four, could be integrated into one or more electronic devices, realized in ASIC (Application-Specific Integrated Circuit), and in that said processor is an FPGA (Field Programmable Gate Array).

Advantageously according to the invention, said sensor portion of said containment enclosure could comprise a door coupled or hinged to said containment enclosure that can be opened and closed.

Always according to the invention, said sensor module could comprise a base, arranged partially below said printed circuit board, in correspondence of said input connector, on said base being obtained a guide, which is insertable in said support, and a blocking element, which forms with the latter a housing (35), in which said input connector is placed.

Still according to the invention, said base of said detecting module could have a first longitudinal groove, intended to house a first seal, arranged in contact with a first face of said printed circuit board, and said blocking element of said detection module could have a second longitudinal groove, intended to house a second seal, arranged in contact with a second face, opposite to said first face of said printed circuit board.

Further according to the invention, said base and/or said blocking element could be made of hydrophobic plastic material.

Advantageously according to the invention, said containment enclosure could have at least one inspection opening to which a microscope for optical control could be applicable and/or through which it is possible to provide solutions for performing experiments and measurements.

Always according to the invention, said inspection opening could be obtained in said sensor portion, below said base, and in that said base could have further opening arranged in correspondence of said inspection opening.

Still according to the invention, said support could be double layer type, comprising an upper layer, having a plurality of main holes, a common hole and a series of superficial contacts, and a lower layer, on which a plurality of electrodes are arranged, each arranged in a respective main hole of said upper layer, each one of said electrodes being connected to one respective of said sensors, and a further common electrode, arranged in correspondence of said common hole, said electrodes and said common electrode being connected to said superficial contacts.

Advantageously according to the invention, when said support is inserted in said guide of said base, each one of said superficial contacts could came in contact with a corresponding terminal of said input connector.

Further according to the invention, said detection device could comprise electromagnetic shielding means.

Always according to the invention, said shielding means could be arranged close to or on said one or more electronic devices and are connected to a common potential different from said analogical ground and/or said digital ground, preferably said common potential is comprised between 1 Volt and 2 volts, more preferably equal to about 1.65 Volts, so as to maximize the shielding effect, said common potential being used internally to said one or more electronic devices in which said processing channels are integrated as a reference for all other voltages of said detection device.

Still according to the invention, said processing module could comprise an analogical ground and a digital ground.

Further according to the invention, said electromagnetic shielding means could comprise a ferrite for the connection between said analog ground and said digital ground, said containment enclosure being connected to said analog ground.

Advantageously according to the invention, said input connector and said analog part of said processing channels could be enclosed by a analogical ground plane on an inner layer of said printed circuit board, which constitutes said analog ground or are connected to a common potential, and said shielding means comprise a first metal or Faraday cage, and the digital part of said processing channels and said processor could be enclosed by a digital ground plane within the printed circuit board, which constitutes said digital ground, and said shielding means comprise a second Faraday cage above and below said printed circuit board.

The present invention will be now described, for illustrative but not limitative purposes, according to its preferred embodiments, with particular reference to the figures of the enclosed drawings, wherein.

In the various figures, similar parts will be indicated by the same reference numbers.

Referring to FIGS. 1-4, it is seen a high sensitivity multichannel detection device 1 according to the invention, essentially comprising a processing module 2, and a detection module 3, connected to said processing module 2, both arranged in a containment enclosure 11. Said containment enclosure 11 is preferably made of metal and has a body 12 and a sensor portion 13, which provides a door 14, coupled with said containment casing 11 and possibly hinged to it.

The processing module 2 comprises a processing unit 4 placed in the body 12 of said containment enclosure 11, provided with a printed circuit 41, in which an input connector 42 is arranged. Said input connector 42 is in its turn provided with a plurality of terminals 42' of the spring-type. Said processing unit 4 also includes an output connector 43 of USB-type, for the connection of the device 1 to a personal computer or processor.

Figure 1:
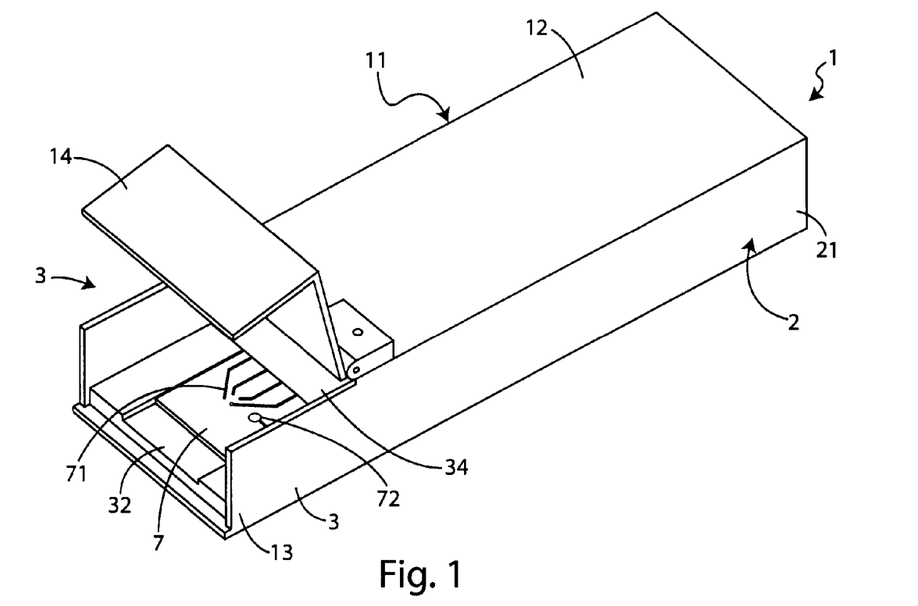
FIG. 1 shows a perspective overall view of a high sensitivity multichannel detection device according to the present invention.
Figure 2:
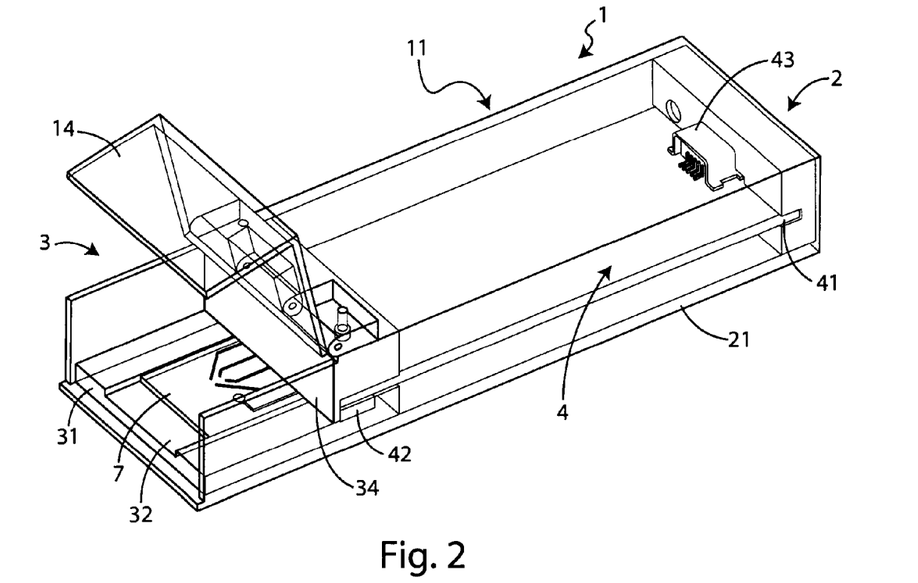
FIG. 2 shows a perspective view in transparency of the device according to FIG. 1.
Figure 3:
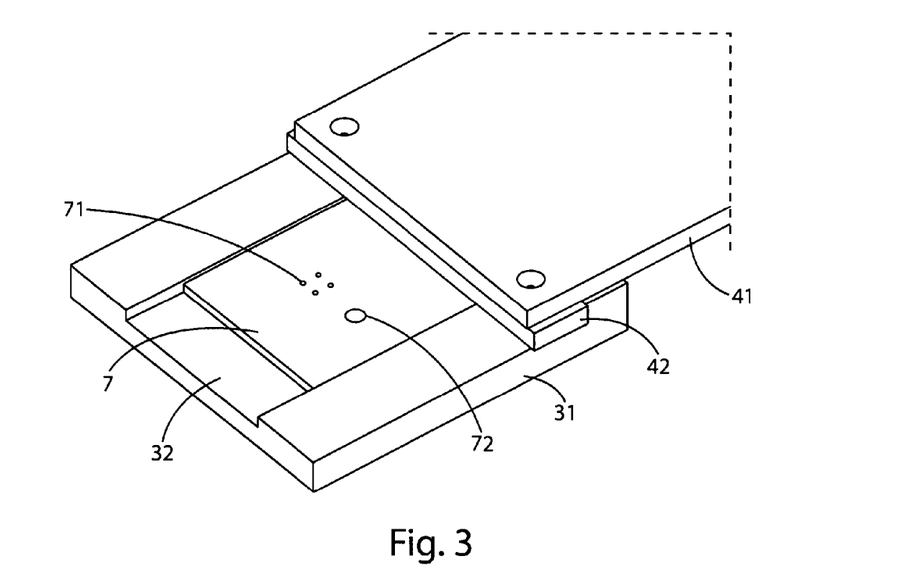
FIG. 3 shows a seat for the insertion of a sample to be examined in the device according to FIG. 1.
Figure 4:
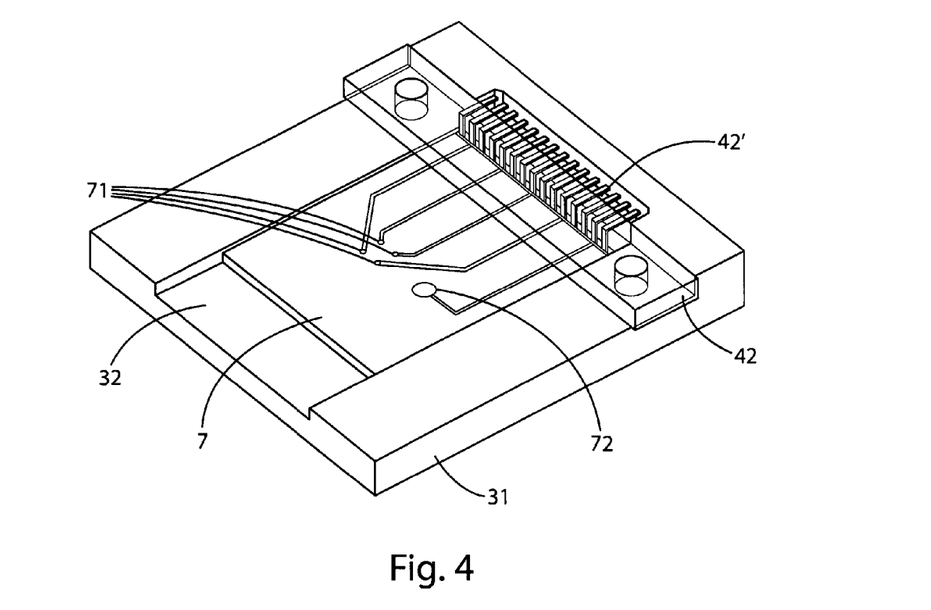
FIG. 4 shows a detail of an electrical connector of the device according to FIG. 1.
Figure 5:
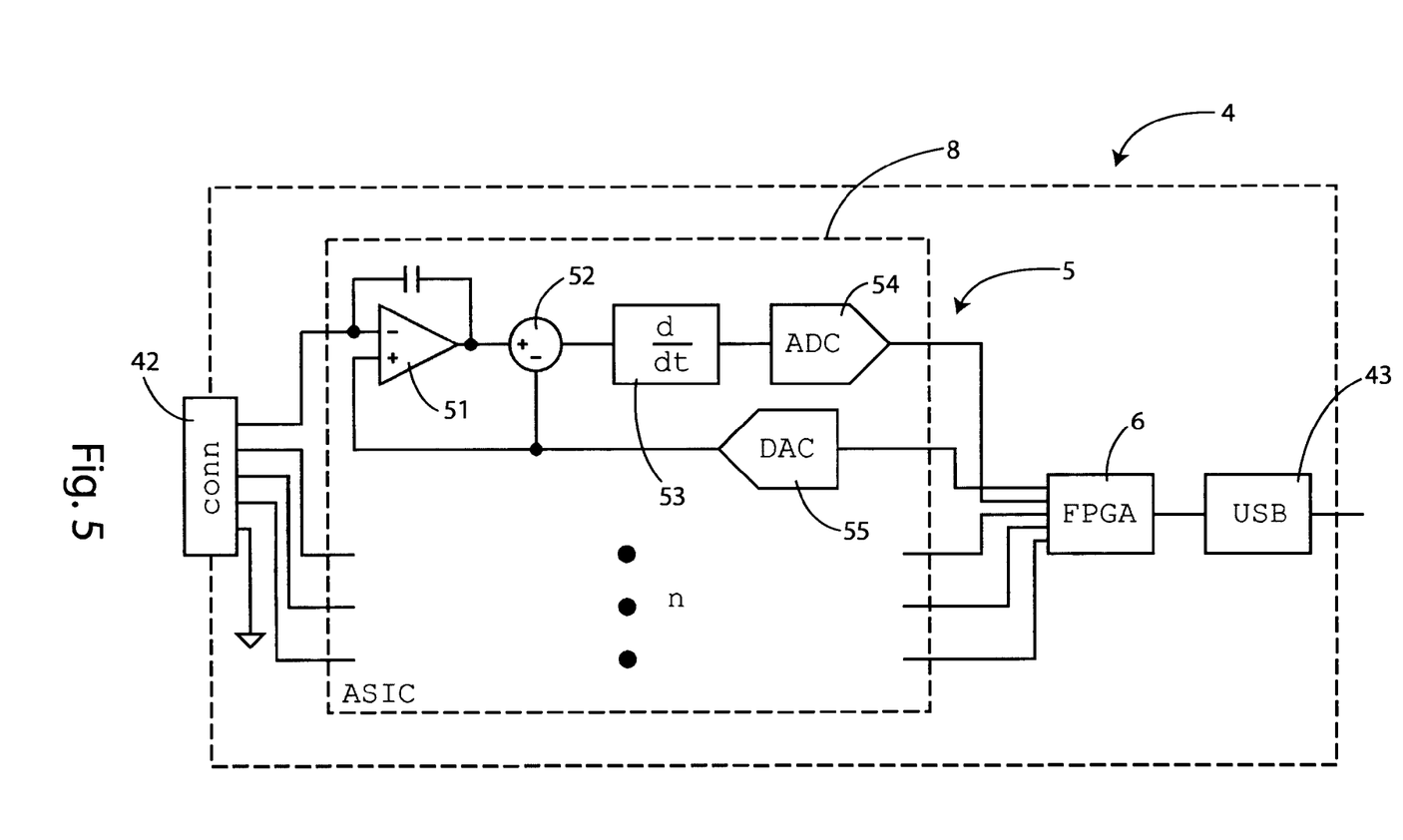
FIG. 5 shows the circuit diagram of the detection device according to the present invention.

Said processing unit 4, whose processing circuit diagram is shown in FIG. 5, also includes four processing channels 5 (in FIG. 5 the diagram of a single processing channel 5 is shown) and a processor 6, connected in output to said output connector 43.

Each one of said processing channels 5 comprises an amplifier 51, preferably an operational amplifier having its inverting input connected to said input connector 42, an adder 52, interposed between said amplifier 51, and a differentiator 53 or high-pass active filter. Connected to said differentiator 53, said processing channel 5 comprises an analog/digital converter 54, having its output connected to said processor 6. Finally, each of said processing channels 5 comprises a second digital/analog converter 55, having the input connected to said processor 6 and the output connected both to said adder 52, in the inverting terminal, and in input to said amplifier 51, to the non-inverting terminal.

The processing channels 5, which in this case are four, are integrated in a single electronic device, made as an ASIC (Application Specific Integrated Circuit), while said processor 6 is a FPGA (Field Programmable Gate Array), i.e. an integrated circuit whose features are programmable by software.

FIG. 5 also shows the schematic arrangement of a Faraday cage 8 (see the dashed line), which protects the four processing channels 5 of the detection device 1.

The above enables to minimize interference from outside and interference from the digital circuitry of the processor 6. In other words, the Faraday cage 8 allows to obtain the signal to noise ratio (S/N) appropriate and necessary to discriminate signals otherwise hidden by noise.

The detection device 1 includes, in a preferred embodiment, shielding means, and is provided for the separation between analog ground and digital ground, connected each other together by means of a ferrite core (not shown in the figure). Furthermore, the external containment enclosure 11 is connected to the analog ground.

The input connector 42 with terminals 42' of spring type and the elements of the analog processing channels 5 (i.e. the amplifier 51, the adder 52 and the differentiator 53) are enclosed by an analog ground plane, on an inner layer of the printed circuit 41 where electronics is mounted. It is also provided a metal cage above, i.e. the aforementioned Faraday cage 8, so as to totally enclose the sensitive part with a shield to the analog ground. More particularly, said Faraday cage can be connected to a common fixed potential, different from said the analog ground and/or to said digital mass, preferably comprised between 1 Volt and 2 volts, more preferably equal to about 1.65 Volts. Said common potential, which is connected to said Faraday cage, is used internally of the electronic device, in which said processing channels 5 are integrated and is used as a reference for all other voltages of the detection device 1. The chosen value of 1.65 indicated Volts equals or Vdd/2, i.e. to half of the power supply potential of said electronic device.

All of the digital part of the processing channels 5 (i.e. the Analog/Digital converter 54 and the second Digital/Analogue converter 55) and said processor 6 are connected, in a similar way, from a digital ground plane to the printed circuit 41.

It is considered that for reading signals of so small intensity is necessary to adopt such special technique of shielding (shielding), it is not sufficient a simple separation of the masses (grounding).

Experimentally, in fact, it was observed that only optimizing the shielding, the performances required for this type of systems (low-noise readout) are obtained. In particular, by placing appropriately said Faraday cage 8 in direct contact with said electronic device, made in ASIC technology the desired signal/noise ratio characteristics are obtained.

Furthermore, this particular shielding turns out to be at an analog potential different from one of the two masses (both analog and digital). This differentiates the system concerned by normal grounding systems. This shielding technique can be extended to all applications that use low-noise readout chip with mixed signals (mixed analog/digital signal).

The sensing module 3 is arranged in the portion of the sensor 13 of the containment enclosure 11, in correspondence of said door 14, and internally comprises a base 31, arranged partially below said printed circuit board 41, at said input connector 42, and a blocking element 34 partially overlapped on said base 31, which form with the latter a housing 35, into which said input connector 42 is placed.

On said base 31 a guide 32 is obtained, which is insertable in a double-layer support 7 for a sample to be analyzed. Said double-layer support 7 comprises an upper layer, having four main holes 71, a common hole 72 and a set of superficial contacts 73; and a lower layer, on which four electrodes are arranged (not shown in the figures), each arranged in correspondence with a respective main hole 71, and a further and common electrode (not shown in the figures), arranged in correspondence with said common hole 72.

The array of electrodes mentioned above are respectively connected to an array of sensors or biosensors and/or nanosensors, which come into contact with the sample to be examined or measured, as a result of the arrangement on said double-layer support 7 of the same sample to be examined (not shown in the figures), possibly also in liquid form or in solution.

Naturally, said electrodes are connected to corresponding superficial contacts 73. When the double-layer support 7 is completely inserted in said guide 32, each one of the superficial contacts 73 come into contact with a corresponding terminal 42' of said input connector 42.

The operation of the high sensitivity multichannel detection device 1 described above is as follows.

Preliminarily, some drops of a solution of which carrying out the analysis is necessary, such as solutions containing specific single molecular species or drugs of interest, is placed on said double-layer support 7. In this way, due to microfluidity phenomena, e.g. by capillarity, said solution passes through or is in contact with sensors or nanosensors, such as proteins, ion channels, cells and the like. Consequently, appropriate electrical signals are detectable on the electrodes corresponding to the holes 71 and 72 and, therefore, on said surface contacts 73.

When the double-layer support 7 is inserted in the guide 32 (see also FIGS. 6 and 7), after opening said door 14, the electrodes are inserted below said input connector 42, so that said terminals 42' can be in contact with said superficial contacts 73.

Figure 6:
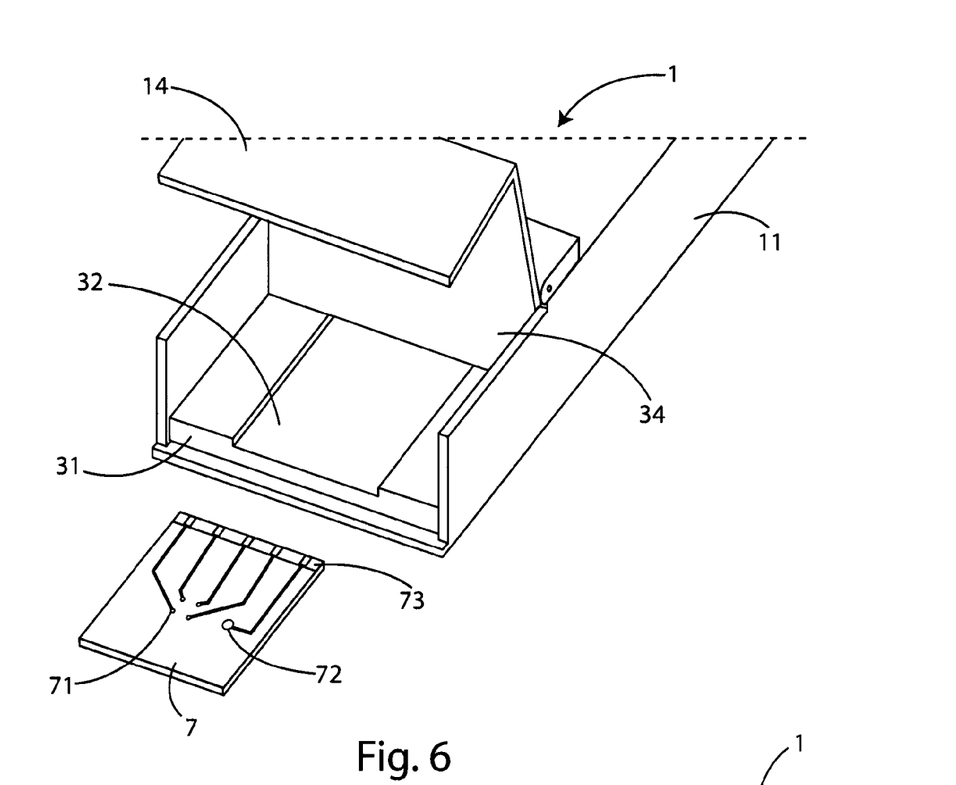
FIGS. 6 and 7 show the steps for inserting a support for a sample to be analyzed in a multichannel detection device according to the invention.
Figure 7:
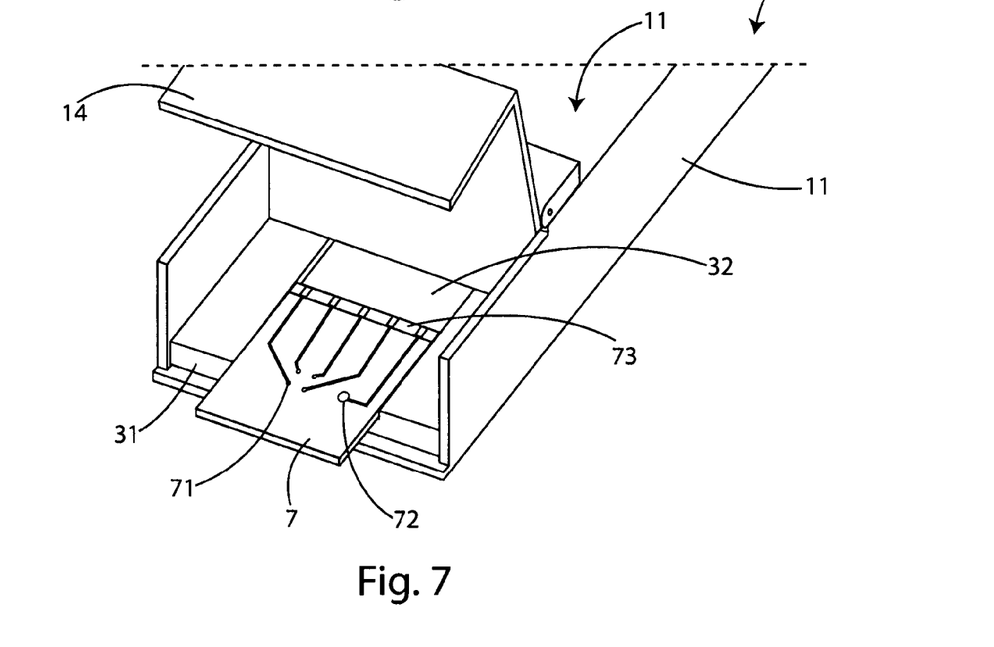

Subsequently said door 14 is closed so as to protect the sample from the surrounding electromagnetic environment.

The detected signals of said terminals 42' of the input connector 42 are amplified by said amplifier 51, filtered by said differentiator 53 and converted by said Analog/Digital converter 54, to be subsequently processed by said processor 6. Once carried out the different (in this case four) measures and obtained the characteristic responses of each biosensor, result signals can be easily detected by said output connector 43.

Figure 8:
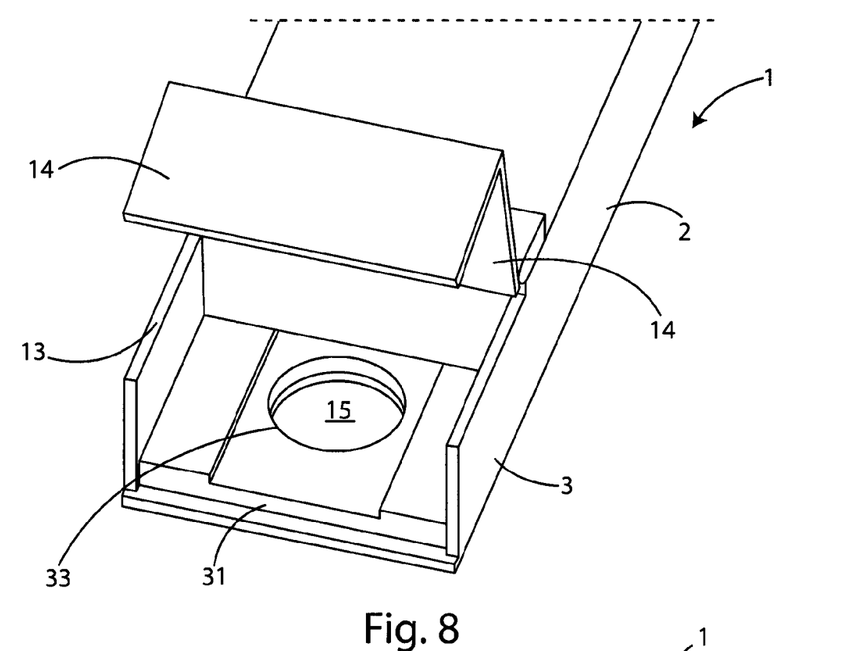
FIG. 8 shows a perspective assembly view of a second embodiment of a high sensitivity multichannel detection device according to the present invention.
Figure 9:
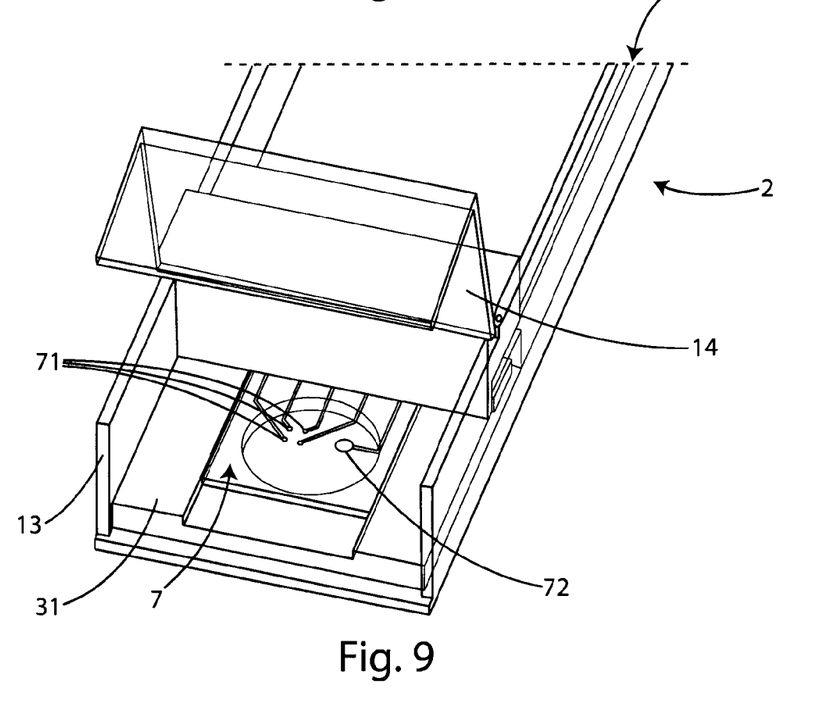
FIG. 9 shows the detection device into which a support for a sample to be analyzed is inserted.

FIGS. 8 and 9 show a second embodiment of the detection device 1, in which the containment enclosure 11 has a circular opening 15 obtained in the portion of the sensor 13, under the base 31. In addition, also the base 31 has a circular opening 33, arranged in correspondence with said opening 15.

These apertures 15 and 33 allow the viewing by a microscope, allowing to have a small system (and therefore easily interfaced to different experimental setups) that allows a double investigation by analyzing simultaneously both the electrical properties and the optical one of the possible biosensor object of study.

Figure 10:
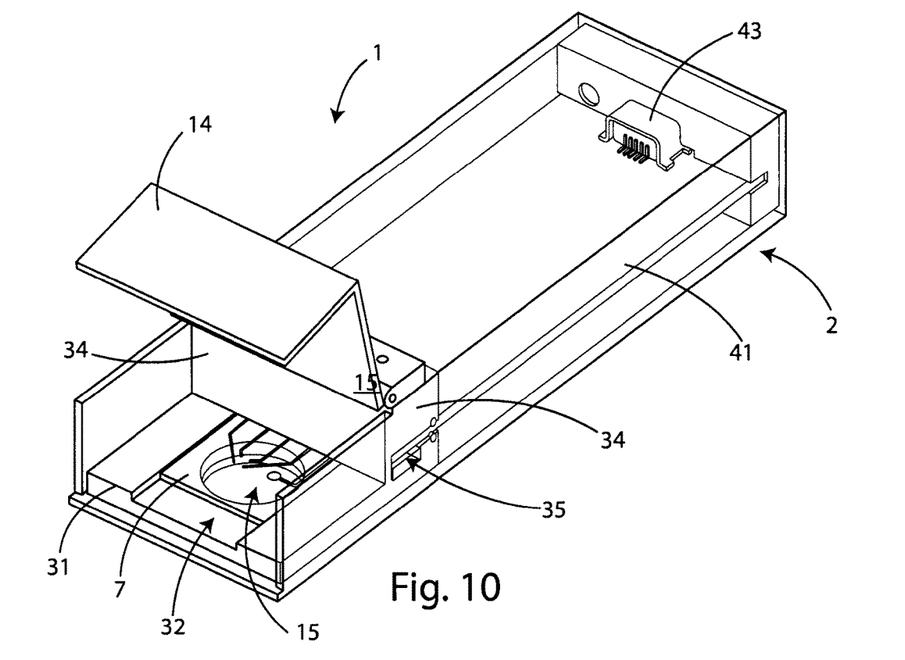
FIG. 10 shows a perspective assembly view of a third embodiment of a high sensitivity multichannel detection device according to the present invention.
Figure 11:
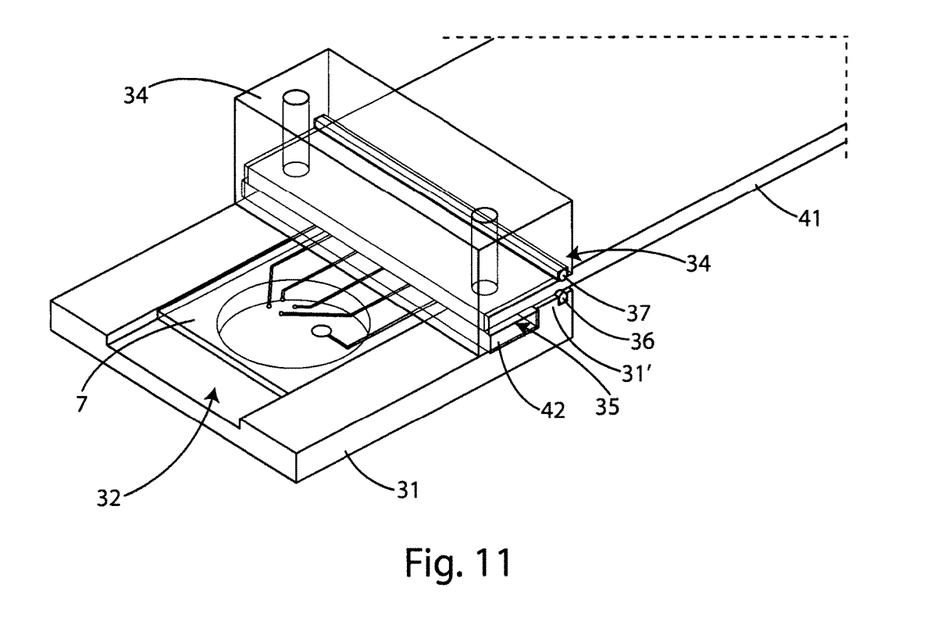
FIG. 11 shows a view in transparency of a detail of the detection device according to FIG. 10.

Referring now to FIGS. 10 and 11, a high sensitivity multichannel detection device 1 is shown, in which there is a particular structure intended to prevent the infiltration of the test solution, placed on the double-layer support 7.

In particular, the base 31 of said detection module 3 has a first longitudinal groove 31', intended to house a corresponding first insulating seal 36, preferably made of rubber, which is in contact with the lower face of said printed circuit 41, while the blocking element 34, in its turn, has a second longitudinal seal 34', intended to house a corresponding second insulating seal 37, also preferably made of rubber, which is in contact with the upper face of said printed circuit board 41.

Said first longitudinal groove 31' and said second longitudinal groove 34' can possibly be arranged parallel and overlapping.

Among other things, said base 31 and said blocking element 34 are made of hydrophobic plastic material, so as to prevent any infiltration.

Using the assembly described, there is a high degree of prevention of the infiltration of liquids and solutions deposited on said double-layer support 7 toward the electronic components mounted on the printed circuit uprights 41.

An advantage of the present invention is that the integration of the circuits of the processing channels 5 in a single chip made by ASIC technology together with the presence of the Faraday cage, allows to obtain a very high level of sensitivity of the instrument.

Another advantage according to the invention is that the described configuration allows to have supports with more than one sensor in a very small space, thereby minimizing the parasitic capacitances on the lines of measurement, and consequently the measurement noise that is proportional.

It is also advantage of the present invention the minimization of parasitic capacitance on the input line so as to read signals of the order of pA (or nA) from different types of sensors, in addition to the possibility of more contemporary measures and in real time.

It is further advantage of the present invention, the portability of the detection device, in addition to not necessity of an external power supply and the use of the same device with different sensor systems also interchangeable.

The present invention has been described for illustrative but not limitative purposes, according to its preferred embodiments, but it is to be understood that modifications and/or changes can be introduced by those skilled in the art without departing from the relevant scope as defined in the enclosed claims.

The invention claimed is:

1. A detection device of a sample to be examined, comprising
a processing module,
a detecting module, connected to said processing module,
a support, in which said sample to be examined can be placed, said support comprising a plurality of sensors and being insertable within said detecting module, and
a containment enclosure comprising a body, which is arranged within said processing module, and a sensor portion, in which said detecting module is arranged,
wherein said processing module comprises a processing unit having a plurality of processing channels and a processor, each processing channel of said plurality of processing channels being connected to one respective sensor of said plurality of sensors and being configured to amplify and to filter the signals of said sensors, said processor processing said signals amplified and filtered by said processing channels, said processing module is placed in said body of said containment enclosure, is provided with a printed circuit board, in which an input connector is arranged, which has a plurality of terminals, and an output connector connected to said processor, for the connection to a personal computer or processor,
wherein said detecting module comprises a base, arranged partially below said printed circuit board, in correspondence of said input connector, on said base being obtained a guide, which is insertable in said support, and a blocking element, which forms with the latter a housing, in which said input connector is placed,
and wherein the support, the housing and the detecting module are fully enclosed inside the body of the containment enclosure.

2. The detection device according to claim 1, wherein each processing channel of said plurality of processing channels comprises
an analog part, which includes an amplifier having an input connected to said input connector, an adder, interposed between said amplifier and a differentiator or active high-pass filter, and
a digital part, which includes an analog to digital converter, having its output connected to said processor, and a second digital to analog converter, having its input connected to said processor and the output connected both to said adder, and to the input of said amplifier, so as to realize a control system of a voltage applied to the input connector.

3. The detection device according to claim 2, wherein
said detection device comprises electromagnetic shielding means;
said input connector and said analog part of said plurality of processing channels are enclosed by an analog ground plane on an inner layer of said printed circuit board, which constitutes said analog ground or are connected to a common voltage, and said electromagnetic shielding means comprise a first metal or Faraday cage, and
the digital part of said plurality of processing channels and said processor are enclosed by a digital ground plane within the printed circuit board, which constitutes said digital ground, and said shielding means comprise a second Faraday cage above and below said printed circuit board.

4. The detection device according to claim 1, wherein processing channels of said plurality of processing channels are integrated into one or more electronic devices, realized in ASIC (Application-Specific Integrated Circuit), and in that said processor is an FPGA (Field Programmable Gate Array).

5. The detection device according to claim 4, said detection device further comprising electromagnetic shielding means.

6. The detection device according to claim 5, wherein said electromagnetic shielding means are arranged close to or on said one or more electronic devices and are connected to a common voltage different from analog ground and/or digital ground, said common voltage being adopted as a reference voltage for all other voltages of said detection device internally to said one or more electronic devices in which said plurality of processing channels are integrated.

7. The detection device according to claim 1, wherein said sensor portion of said containment enclosure comprises a door coupled or hinged to said containment enclosure that can be opened and closed.

8. The detection device according to claim 1, wherein
said base of said detecting module has a first longitudinal groove, intended to house a first seal, arranged in contact with a first face of said printed circuit board, and
wherein said blocking element of said detecting module has a second longitudinal groove, intended to house a second seal, arranged in contact with a second face, opposite to said first face of said printed circuit board.

9. The detection device according to claim 1, wherein said base and/or said blocking element are made of hydrophobic plastic material.

10. The detection device according to claim 1, wherein said containment enclosure has at least one inspection opening.

11. The detection device according to claim 10, wherein said at least one inspection opening is obtained in said sensor portion, below said base, and said base has a further opening arranged in correspondence of said at least one inspection opening.

12. The detection device according to claim 1, wherein said support is a double layer support, comprising an upper layer, having a plurality of main holes, a common hole and a series of superficial contacts, and a lower layer, on which a plurality of electrodes are arranged, each electrode of said plurality of electrodes being arranged in a respective main hole of said upper layer, each electrode of said plurality of electrodes being connected to one respective sensor of said plurality of sensors, and a further common electrode, arranged in correspondence of said common hole, said electrodes and said common electrode being connected to said series of superficial contacts.

13. The detection device according to claim 12, wherein when said support is inserted in said guide of said base, each superficial contact of said series of superficial contacts comes into contact with a corresponding terminal of said input connector.

14. The detection device according to claim 1, wherein said processing module comprises an analog ground and a digital ground.

15. The detection device according to claim 14, said detection device further comprising electromagnetic shielding means, wherein said electromagnetic shielding means comprise a ferrite for connection between said analog ground and said digital ground, said containment enclosure being connected to said analog ground.

16. The detection device according to claim 1, said detection device further comprising electromagnetic shielding means.

17. The detection device according to claim 1, wherein:
(i) the input connector is placed inside the body closer to a first end of the body than a second end of the body;
(ii) the output connector is placed at the second end of the body; and
(iii) the first end and the second end of the body are opposite ends of the body.

* * * * *